United States Patent [19]

Lange-Mickel et al.

[11] Patent Number: 5,697,786
[45] Date of Patent: Dec. 16, 1997

[54] DENTAL FLUID SUCTION UNIT AND METHOD FOR ITS MANUFACTURE

[75] Inventors: Gertrud Lange-Mickel, Winnenden; Paul Mörsch, Michelbach/Bilz; Gebhard Wahl, Winnenden, all of Germany

[73] Assignee: Albert Eger GmbH & Co., Winnenden, Germany

[21] Appl. No.: 640,835

[22] PCT Filed: Jan. 21, 1995

[86] PCT No.: PCT/DE95/00087

§ 371 Date: May 1, 1996

§ 102(e) Date: May 1, 1996

[87] PCT Pub. No.: WO95/20364

PCT Pub. Date: Aug. 3, 1995

[30] Foreign Application Priority Data

Jan. 26, 1994 [DE] Germany .................. 44 02 142.9

[51] Int. Cl.⁶ .................................................. A61C 17/06
[52] U.S. Cl. ...................................... 433/96; 493/269
[58] Field of Search ................... 433/96, 269; 239/33

[56] References Cited

U.S. PATENT DOCUMENTS 2,094,568  9/1937  Friedman ........................ 239/33
2,327,337  8/1943  Gibbin ............................. 433/96
3,025,004  3/1962  Levi ................................. 239/33
3,339,004  8/1967  Nardone ......................... 493/269
5,476,630  12/1995  Orsing ............................ 433/96

FOREIGN PATENT DOCUMENTS 9216033  1/1993  Germany .

*Primary Examiner*—John J. Wilson
*Attorney, Agent, or Firm*—Paul Vincent

[57] ABSTRACT

A flexible paper tube, in particular a throw-away saliva suction unit for dentistry, comprises two tubular sections integrally connected to each other via a bellows and is characterized in that the paper tube (2, 6) is constructed from multi-layer paper, in particular having 3 through 15 layers and preferentially 4 to 10 layers of thickness 0.07 to 0.35 mm, in particular 0.1 to 0.2 mm and with a wall thickness between 0.2 to 2.5 mm, preferentially 0.5 to 1 mm. The fluting and folding of the bellows is preferentially done before hardening of the glued paper layers. The paper tube (2, 6) in accordance with the invention guarantees that the tube passage is not reduced in size when flexing of the tube through bending of the bellows.

20 Claims, 1 Drawing Sheet

1

DENTAL FLUID SUCTION UNIT AND METHOD FOR ITS MANUFACTURE

BACKGROUND OF THE INVENTION

The invention concerns a flexible paper tube, in particular a throw-away saliva suction unit for dentistry, comprising two tubular sections integrally joined with another via a bellows.

A paper tube of this type is known in the art from German utility model G 92 16 033.6.

Tubes having cylindrical sections integrally joined to another via a bellows have been used for some time by dentists during dental treatments in order to extract saliva from the oral cavity of the patient through one of the tubular sections with the assistance of a vacuum device connected to the other tubular section in order to prevent flooding of the oral cavity with saliva and to guarantee proper visual working conditions for the dentist. These types of saliva suction or vacuum units must be water resistant at least for a certain period of time to prevent soaking-through during the treatment time of the patient. In addition the bellows located in the mid-region of the saliva suction unit must facilitate flexibility of the device in order to bring the suction tubular end into the region of the floor of the mouth of the patient from above with the vacuum device being arranged at the side and usually below the patient. This can only be achieved by bending the bellows through a relatively large bending angle.

For reasons of structural integrity, conventional saliva vacuums have utilized, up to this time, either a metal tube or plastic tube with associated bellows. Metallic saliva vacuum units had the disadvantages of being costly, and nevertheless of limited life-time and are associated with the difficulties and expenses of cleaning, disinfecting, and sterilizing. Plastic saliva suction units which, for hygienic reasons, could be utilized as throw-away articles were, in contrast thereto, less expensive, however had problems related to disposal thereof.

Cardboard throw-away saliva suction units had already been used more than 50 years ago at a time when plastic was not yet of today's quality nor available at today's usually low prices which, however, had wire inlays in their walls to substantially maintain the tube passage along the entire length of the saliva suction unit when the tube was bent. The wire insert caused this type of saliva suction unit made from cardboard or fibre materials to be relatively expensive to manufacture and did not present a substantial improvement with regard to the disposal problem in comparison to corresponding modern throw-away saliva suction units made from plastic.

The saliva suction unit described in the above mentioned utility model G 92 16 033.6 made from paper maché, statuary paste board, pressboard, cardboard or paper materials was intended to be manufactured by forming and/or pressing in a cardboard mould and subsequent shaping into a tube. It was already envisioned that a section of the tube be formed as a bellows to give the tube a certain amount of flexibility so that the tube was bendable or foldable in the bellows region without reducing the cross sectional passage of the tube.

This, however, was only possible in the device described in this publication when a stiffening of the tube walls was provided by means of a wire insert since otherwise the single layer tube would fold-up in the bellows region or an appropriate bellows could simply not be manufactured using a single layer tube made from paper maché, statuary paste board, pressboard, cardboard or paper materials.

It is therefore the purpose of the present invention to present a flexible paper tube of the above mentioned type which guarantees full maintenance of the tube passage without wire inserts when flexing the tube through bending of the bellows.

SUMMARY OF THE INVENTION

This purpose is achieved in accordance with the invention in that the paper tube is constructed from multi-layer paper, in particular having 3 through 15 layers and preferentially 4 through 10 layers with thickness of 0.07 mm to 0.35 mm, in particular 0.1 to 0.2 mm and having a wall thickness between 0.2 to 2.5 mm, preferentially 0.5 to 1 mm.

Surprisingly the multi-layer configuration of paper layers in accordance with the invention, which actually leads to a stiffening of and therefore reduction in the required flexibility of the paper tube, turns out to actually facilitate the flexibility of the paper tube without using wire inserts, since, by means of the measures in accordance with the invention, not only the tubular sections, but also the bellows itself is stiffened in such a manner that a folding-over and associated drastic reduction in the tube passage opening of the tube is prevented when the bellows is bent. The values mentioned for the paper thickness of the individual layers, the number of layers as well as the wall thickness of the paper tube have been shown to be particularly advantageous for satisfying the intrinsically contradictory requirements of high stiffness and simultaneous large flexibility of the tube.

An embodiment of the paper tube in accordance with the invention is particularly preferred with which the paper layers contain long fibre pulp having a high degree of beating with fibres whose length is mostly 5 mm and longer. The relatively long fibers and the high degree of beating cause a large degree of interlacing of the fibers so that good elasticity with concurrent high stability of the material is achieved. Paper maché or cardboard material is, in contrast thereto, of short-fiber construction and therefore breaks relatively easily so that neither the required tube stability nor the required flexibility can be achieved.

In a further embodiment of the paper tube in accordance with the invention, the paper layers are, in particular, wound in parallel from a blank of finite length. This has the advantage that the stability of the tube is particularly high. A certain lack of roundness of the tube must however be accepted since the parallel-wound blank has a beginning and an end which causes a radial asymmetry of the wound tube.

In another embodiment, the paper layers are spirally wound, endless material. In this case the paper tube can be manufactured in nearly a perfectly round state however with somewhat reduced stability.

An embodiment of the paper tube in accordance with the invention is particularly preferred for the intended purpose of dentistry with which the inner and outer surface is coated with water-resistant or water-repellent material. Alternatively the paper tube can be constructed from the outset using water-resistant paper layers. In this fashion, one guarantees that a throw-away saliva suction tube of this kind does, in any event, not soak through during a treatment.

Embodiments are possible in which a perforated cap is provided for placement onto one of the tubular sections in particular for the application as a throw-away saliva suction unit to prevent a suctional attachment of the tubular section located in the patient's mouth and associated interruption of the saliva suctioning.

A cap of this type is particularly inexpensive to manufacture when it is made from the same material as the flexible paper tube in accordance with the invention. A high structural integrity of the cap can be achieved, in particular, with multi-layer configuration of the paper layers.

In embodiments of the invention the paper tube has a length to inner diameter clearance ratio between 5 and 25, preferentially between 10 and 20, and in particular, approximately 15. The bellows can be symmetrically or asymmetrically located between the two tubular sections.

An embodiment of the paper tube in accordance with the invention is particularly preferred with which the bellows is sufficiently long to allow the tubular sections connected to each other by means of the bellows to be able to be brought into a position in which they are parallel to each other by folding of the bellows through approximately 180°. In this fashion, in particular for use as a throw-away saliva suction unit, any arbitrary configuration of the vacuum device relative to the patient can be chosen.

A method for the manufacture of a flexible paper tube of the above mentioned kind is also within the framework of the invention, the method being characterized in that:

during a first manufacturing step, a cylindrically shaped paper tube is wound on a winding device using thin multi-layered paper and each layer is glued to its neighbouring layer;

in a second manufacturing step, the multi-layered paper tube is, with the assistance of two centering bushings arranged on the ends of the paper tube, axially aligned and radially centered on a fluted arbor of a fluting device having, along its axial length, a smooth, a fluted and a further adjacent smooth region, set into rotation about its longitudinal axis together with the fluted arbor, pressed against the fluted region of the fluted arbor by means of a radial stroke of at least one fluted roller arranged axially parallel to the fluted arbor, and stripped from the fluted arbor after withdrawal of fluted roller; and in a third manufacturing step, the fluted multi-layer tube is positioned on a folding arbor and, by means of clamping rings arranged on both sides of the fluted region of the paper tube, clamped onto two additional centering bushings each extending from the end of the paper tube in the axial direction up to the clamping rings, folded up in the fluted region through axial squeezing together of the two additional centering bushings, and finally stripped from the additional centering bushings after removal of the clamping rings.

In a particularly preferred variation of the method in accordance with the invention at least the second and preferably also the third production step is carried out prior to hardening of the neighbouring paper layers glued in the first production step.

It is particularly preferred when the residual dampness of the paper tube in the second, preferentially however also in the third manufacturing step is in excess of 20%, preferably 30% through 40%. In this fashion production of the fluting as well as of the bellows on the paper tube is facilitated without having the material breaking due to excessive brittleness.

In a further variation of the method, the stripping of the paper tube in the second and third manufacturing steps is effected by a removal of the paper tube from the fluted arbor or from the folding arbor respectively. In order to prevent a premature folding or damaging of the paper tube at the end of the second manufacturing step, the tube must not be pushed-off the fluted arbor. At the end of the third manufacturing step, the then already folded paper tube must likewise not be pushed-off of the folding arbor during stripping, rather pulled-off in order to prevent jamming of the folded paper bushing.

In order to keep the radial forces on the tube as small as possible during the radial motion of the fluted roller, it is preferred, during the second manufacturing step, to utilize a plurality of, in particular three or four, fluted rollers which are symmetrically arranged around the circumference of the fluted arbor. When using only two fluted rollers positioned opposite to each other, a misalignment of the fluted arbor and the paper tube in a direction perpendicular to the plane connecting the fluted rollers can occur. This is avoided through the use of three or more fluted rollers.

It is preferred when differing, exchangeable sets of fluted arbors and associated fluted rollers having differing numbers, and/or arrangement, and/or separation, and/or depth of the grooves are provided for use in the second manufacturing step so that grooves and corresponding bellows having differing geometries can be produced.

In a preferred variation of the method, the inner diameter of the paper tube is chosen in such a fashion with respect to the outer diameter of the fluted arbor that a flattening of the grooves produced on the paper bushing in the second manufacturing step is avoided when stripping same from the fluted arbor.

In a particularly simple variation of the method, the fluted rollers can be free-running and assume a corresponding peripheral velocity when radially pressed against the paper tube.

In accordance with another variation of the method, the fluted rollers can be driven with the assistance of a motor.

A variation of the method is preferred with which, in the second manufacturing step, the peripheral velocity of the outer diameter of the paper tube is chosen by appropriate adjustment of the rotational velocity of the fluted arbor, to be equal to the peripheral velocity of the fluted rollers so that there is no mutual transfer of forces onto the drive bearings of the rotational motors.

A variation of the method is also preferred with which the inner diameter of the bushing tube, the number, the arrangement and the depth of the grooves produced in the second manufacturing step as well as the outer diameter of the folding arbor are chosen in such a fashion that the bellows region of the paper tube folded in the third manufacturing step is in contact with the folding arbor around the entire circumference. A sideward displacement of the paper tube can thereby be prevented so that an even folding is achieved in the third manufacturing step.

Finally, in an additional advantageous variation of the method the ratio of groove depth to groove separation is chosen in the second manufacturing step to be within the range of 1:2 through 1:5.

Further features and advantages of the invention can be derived from the following description of an embodiment of the invention in relation to the drawings showing details which are important to the invention, as well as from the claims. The individual features can be utilized individually or collectively in arbitrary combination with embodiments of the invention.

DESCRIPTION OF THE PREFERRED EMBODIMENT

Figure 1:
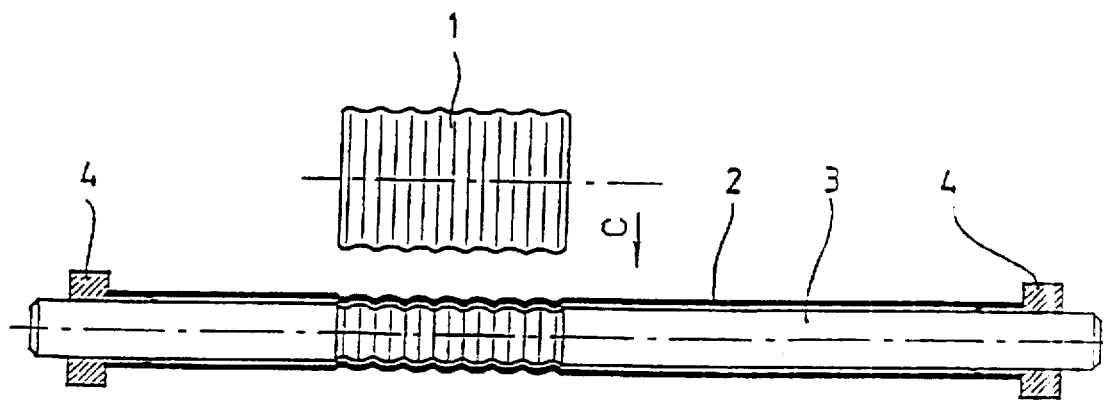
FIG. 1 shows a schematic cut view of the fluting device with positioned paper tube for the second manufacturing step.

The flexible paper tubes in accordance with the invention which are particularly suited as throw-away saliva suction units in dentistry and, in the final state, consist of two tubular sections integrally attached to each other via a bellows, are substantially produced in three steps:

In a first manufacturing step, a cylindrically shaped paper tube made from thin paper is wound in a multi-layer fashion on a winding device not shown in the drawing and each layer is glued to its neighboring layer. Towards this end, at least three layers, preferentially 5 through 10 layers are wound so that the tube attains a corresponding degree of stability with simultaneous flexibility via the bellows produced in the next manufacturing step. Towards this end, paper is utilized which has a thickness of 0.07 to 0.3 mm, preferentially 0.1 to 0.2 mm and a weight between 60 and 240 g/m$^2$. The wall thickness of the paper tube is between 0.2 and 2.5 mm, preferentially between 0.5 and 1 mm.

The paper layers can be wound in parallel from a blank, leading to a particularly high degree of stability of the paper tube. A disadvantage of parallel winding is, however, that the finite blank utilized for the tube has a beginning and an end, leading to a certain lack of roundness of the manufactured paper tube.

Alternatively, the paper layers can be produced with endless paper material using spiral winding techniques to manufacture a paper tube having a perfectly round shape. The spiral winding technique has however the disadvantage of producing tubes which are not quite as strong as parallel wound ones.

In order to give, in any event, the flexible paper tube in accordance with the invention a particularly large degree of stability it is preferable to use paper material containing long fiber pulp having fiber lengths between 3 and 6 mm, with a large fraction of the fibers having a length of 5 mm and more. In addition, a large degree of beating is important for processing of the pulp material to achieve, together with the large fiber length, a large degree of interlacing of the fibers and an associated particularly large stability of the produced paper material.

In a second manufacturing step the multi-layered paper tube 2 manufactured from the first manufacturing step is, as shown in FIG. 1, positioned in an axially aligned and radially centered fashion onto a fluted arbor 3 of a fluting device with the assistance of two centering bushings 4 arranged on the ends of the paper bushing 2. The fluted arbor 3 shown has two flat regions and a grooved region located between these flat regions along the length of which the bellows of the flexible paper tube is subsequently created.

The multi-layer tube 2 is then set into rotation together with the fluted arbor 3 about its longitudinal axis. In the region of the grooves of the fluted arbor 3, at least one fluted roller 1 is arranged axially parallel to the fluted arbor 3 and pressed into the jacket of the multi-layer paper tube 2 from the side by means of a radially stroke in the direction of arrow C. It is preferred when at least three fluted rollers 1 are symmetrically positioned around the periphery of the fluted arbor 3 to keep the radial forces on the fluted arbor 3 as small as possible and to prevent a radial displacement of the fluted arbor 3 along with the multi-layer paper tube 2.

In order to be able to manufacture different types of flexible paper tubes with the same apparatus, differing exchangeable sets of fluted arbors 3 and associated fluted rollers 1 having differing numbers, arrangement, separation and depth of the grooves are envisioned for use in the second manufacturing step. The ratio of groove depth to groove separation is in the range between 1:2 to 1:5.

In a simple embodiment of the fluting device, the fluting rollers 1 can be freely set into rotation about their longitudinal axis when pressed against the rotating paper tube 2, parallel to the fluted arbor 3, in a rotational direction opposite to that of the fluted arbor 3. In a somewhat more complicated fluting device, the fluted rollers 1 are driven with the peripheral velocity of the outer diameter of the paper bushing 2. This can be done either through appropriate adjustment of the rotational velocity of the fluted arbor 3 or through adjustment of the driving velocity of the fluted rollers 1.

After completion of the fluting procedure, the fluted rollers 1 are radially displaced and removed in a direction opposite to that of arrow C from the paper tube 2 and the now fluted paper tube can be stripped from the fluted arbor 3. In order to prevent a premature folding or damaging of the paper tube 2 during stripping from the fluted arbor 3, the paper tube 2 cannot be pushed and the stripping must be carried out by pulling the paper tube 2.

The inner diameter of the paper tube 2 is chosen in relation to the outer diameter of the fluted arbor 3 in such a fashion that a flattening-out of the grooves in the paper tube 2 produced in the second manufacturing step is avoided when stripping same from the fluted arbor 3.

Figure 2:
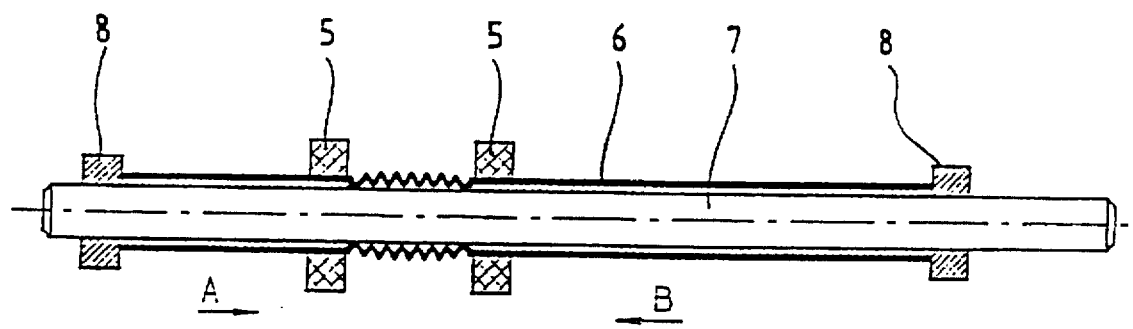
FIG. 2 shows a schematic cut representation of a folding device for the third manufacturing step having a positioned paper tube already folded in the fluted region.

In a third manufacturing step the fluted multi-layer paper bushing 6 is, as shown in FIG. 2, placed onto a folding arbor 7 of the folding device and clamped, using clamping rings 5 arranged on both sides of the fluted region of the paper tube 6, onto two additional centering bushings 8 which each extend in the axial direction from the ends of the paper bushing 6 up to the clamping rings 5, and is folded-up in the fluted region by axially pushing together the additional centering bushings 8 in the direction of arrow A or B.

The inner diameter of the paper bushing 6, the number, the configuration, and depth of the grooves produced in the second manufacturing step as well as the outer diameter of the folding arbor 8 are chosen in such a fashion that the folded bellows region of the paper tube 6 produced in the third manufacturing step is in contact with the folding arbor 7 around its entire periphery. In this fashion, a sideward displacement of the paper tube 6 can be prevented and an even, regular folding of the bellows in the region of the grooves is achieved.

In order to prevent a jamming of the folded paper tube 6 when stripping from the folding arbor 7, the tube cannot be pushed off, rather the stripping must take place by pulling the tube off the additional centering bushings 8 after removal of the clamping rings 5.

At least the second and preferably also the third manufacturing step should be carried out before hardening of the neighbouring paper layers glued in the first manufacturing step so that the paper tube is not too stiff and too brittle for further processing. The residual moisture content of the paper tube 2 or 6 can assume a value in excess of 20%, preferentially between 30% and 40% in the second and third manufacturing step.

Typically, the paper bushing 6 has a ratio of length to inner clearance diameter between 5 and 25, preferentially between 10 and 20. The bellows region of the flexible paper tube should be sufficiently long that the two tubular sections attached to each other by means of the bellows can be brought into a position parallel to each other by bending the bellows through approximately 180°.

In particular for the above mentioned dental application as a throw-away saliva suction unit, the flexible paper tube 2 or 6 in accordance with the invention can be coated on its inner and outer surfaces with a water-resistant or water-repellent material. Water-resistant paper could also be used from the outset for winding the paper bushing in the first manufacturing step.

A perforated cap can be placed on one of the tubular sections to prevent a suctional attachment of the one tubular section of the paper tube in accordance with the invention during use as a throw-away saliva suction unit in the mouth of the patient. The cap can be made from the same material as the flexible paper tube 2 or 6. In particular, it can be, as is the paper tube itself, made from paper having a plurality of layers and be recycled after one-time use along with the flexible paper tube. The cap can also be made from a permanent material for multiple use, in particular from plastic or from metal, preferentially from stainless steel sheet metal.

We claim:

1. A flexible paper tube for use as a throw-away saliva suction unit in dentistry comprising:

a first tubular section;

a second tubular section; and a bellows connected between said first and said second tubular section, wherein the paper tube is constructed from multi-layered paper, layers of said multi-layered paper having a thickness of 0.07 to 0.35 mm, and the tube having a wall thickness of 0.2 to 2.5 mm.

2. The tube of claim 1, wherein said layers comprise long fiber pulp having a fiber length >5 mm and a high degree of beating.

3. The tube of claim 1, wherein said layers are wound in parallel.

4. The tube of claim 1, wherein said layers are spirally wound.

5. The tube of claim 1, further comprising a water-resistant or water-repellent coating on inner and outer surfaces of the tube.

6. The tube of claim 1, wherein the tube is constructed from layers of water-resistant paper.

7. The tube of claim 1, wherein the tube has a ratio of length to inner clearance diameter between 5 and 25.

8. The tube of claim 1, wherein said bellows has a length adapted to allow said first and said second tubular sections to be brought into a position in which they are parallel to each other when bending said bellows through approximately 180°.

9. A method for the production of a flexible paper tube for use as a throw-away saliva suction unit in dentistry, the tube having a first tubular section, a second tubular section and a bellows connected between said first and said second tubular section, the method comprising the steps of:

a) winding, on a winding device, a cylindrically shaped paper tube from paper in a multi-layer fashion and gluing each layer to its neighbouring layer;

b) positioning the tube with the assistance of a first bushing located at a first and a second bushing located at a second end of the tube in an axially aligned and radially centered fashion on a fluted arbor of a fluting device, said fluted arbor having along its axial length a first smooth, a fluted and a second smooth region; rotating the tube and said fluted arbor about a longitudinal axis; arranging a fluted roller to be axially parallel to said fluted arbor; radially pressing said fluted roller against said fluted region of said fluted arbor to produce grooves in a fluted region of the tube; and stripping the tube from said fluted arbor after removal of said fluted roller; and c) placing the tube onto a folding arbor; clamping, by means of a first clamping ring positioned at a first end of said fluted tube region and a second clamping ring positioned at a second end of said fluted tube region, the tube onto a first centering bushing extending from said first tube end to said first clamping ring and onto a second centering bushing extending from said second tube end to said second clamping ring; folding-up said fluted tube region by axially pushing said first and second centering bushings together; and stripping the tube from said first and second centering bushings after removal of said first and said second clamping rings.

10. The method of claim 9, wherein step b) is carried out before hardening of the glued neighbouring paper layers of step a).

11. The method of claim 10, wherein step c) is carried out before hardening of the glued neighbouring paper layers of step a).

12. The method of claim 10, wherein a residual moisture content of the tube in step b) exceeds 20%.

13. The method of claim 9, wherein said stripping of the tube in steps b) and c) is effected by pulling the tube off said fluted arbor and said folding arbor.

14. The method of claim 9, wherein in step b) a plurality of fluted rollers are arranged symmetrically about a circumference of said fluted arbor.

15. The method of claim 9, wherein, in step b), exchangeable sets of fluted arbors and fluted rollers are provided having at least one of differing numbers, differing arrangement, differing separation, and differing depth of grooves in said fluted arbor region.

16. The method of claim 9, wherein an inner diameter of the tube is selected relative to an outer diameter of said fluted arbor to prevent a flattening out of said grooves when stripping the tube from said fluted arbor.

17. The method of claim 9, wherein said fluted roller is free-running.

18. The method of claim 9, wherein said fluted roller is driven and, in step b), a peripheral velocity of an outer diameter the tube is selected by appropriate adjustment of a rotational velocity of said fluted arbor to be equal to a peripheral velocity of said fluted roller.

19. The method of claim 9, wherein an inner diameter of the tube, a number, arrangement, and depth of said grooves, and an outer diameter of said folding arbor are chosen in such a fashion that said bellows is in contact with said folding arbor in step c) around an entire periphery thereof.

20. The method of claim 9, wherein in step b), a ratio of groove depth to groove separation is chosen in a range between 1:2 to 1:5.

* * * * *